United States Patent [19]
Lupski et al.

[11] Patent Number: 5,306,616
[45] Date of Patent: Apr. 26, 1994

[54] MOLECULAR DIAGNOSIS OF AUTOSOMAL DOMINANT CHARCOT-MARIE-TOOTH DISEASE

[75] Inventors: James R. Lupski; Pragna I. Patel; Roberto M. de Oca-Luna; Odila S. Cardenas, all of Houston, Tex.

[73] Assignee: Baylor College of Medicine, Houston, Tex.

[21] Appl. No.: 711,615

[22] Filed: Jun. 6, 1991

[51] Int. Cl.$^5$ .................... C12Q 1/68; C07H 21/04; C12N 15/11
[52] U.S. Cl. ................................ 435/6; 536/23.1; 536/23.5; 536/24.1; 536/24.2; 536/23.2; 935/8; 935/17; 935/78
[58] Field of Search ............... 435/6; 536/27, 23.1, 536/23.2, 23.5, 24.1, 24.2; 935/8, 17, 78

[56] References Cited

PUBLICATIONS

Weber, et al. 1990, Nucleic Acids Research 18:4638.
Bedford, M. T., and van Helden, P. D.; A Method to Analyze Allele-Specific Methylation; BioTechniques 9:744–748 (1990).
Chance, P. F., et al; Genetic Linkage and Heterogeneity in Type I Charcot-Marie-Tooth Disease (Hereditary Motor and Sensory Neuropathy Type I); Am. J. Hum. Genet., 47:915–925 (1990).
Devlin, R. H., et al; Partial Gene Duplication Involving Exon-Alu Interchange Results in Lipoprotein Lipase Deficiency; Am. J. Hum. Genet., 46:112–119 (1990).
Fain, P. R., et al; Genetic Analysis of NF1: Identification of Close Flanking Markers on Chromosome 17; Genomics 1:340–345 (1987).
Franco, B., et al; An MspI RFLPs at the D17S258 locus; Nucleic Acids Research, 18:7196 (1990).
Herrmann, Bernhard G., et al; A Large Inverted Duplication Allows Homologous Recombination between Chromosomes Heterozygous for the Proximal t Complex Inversion; Cell 48, 813–825 (1987).
Kornreich, Ruth, et al; α-Galactosidase A Gene Rearrangements Causing Fabry Disease; The Journal of Biological Chemistry, 265:9319–9326 (1990).
Lawrence, Jeanne Bentley, et al; Interphase and Metaphase Resolution of Different Distances Within the Human Dystrophin Gene. Science, 249:928–932 (1990).
Litt, Michael; A Hypervariable Microsatellite Revealed by in Vitro Amplification of a Dinucleotide Repeat within the Cardiac Muscle Actin Gene; Am. J. Hum. Genet. 44:397–401 (1989).
Lupski, J. R., et al; Charcot-Marie-Tooth Polyneuropathy Syndrome: Clinical, Electrophysiologic, and Genetic Aspects; In Current Neurology S. Appel, ed. (Chicago, Mosby-Yearbook), pp. 1–25 (1991).
Magenis, R. Ellen, et al; De Novo Partial Duplication of 17p [dup(17)(p12-p11.2)]: Clinical Report; American Journal of Medical Genetics 24:415–420 (1986).
McAlpine, P. J., et al; Localization of a Locus for Charcot-Marie-Tooth Neuropathy Type la (CMT1A) to Chromosome 17; Genomics 7, 408–415 (1990).
Middleton-Price, H. R., et al; Linkage of Hereditary Motor and Sensory Neuropathy Type I to the Pericentromeric Region of Chromosome 17; Am. J. Hum. Genet. 46:92–94, 1990.
Nakamura, Y., et al; A Mapped Set of DNA Markers for Human Chromosome 17; Genomics 2, 302–309 (1988).

(List continued on next page.)

*Primary Examiner*—Robert A. Wax
*Assistant Examiner*—Gabriele E. Bugaisky
*Attorney, Agent, or Firm*—Fulbright & Jaworski

[57] ABSTRACT

A method for detecting Charcot-Marie-Tooth (CMT) disease by measuring the presence or absence of a DNA duplication in a gene locus associated with the CMT disease. The method employs extracting DNA from a sample to be tested, and performing Southern analyses with probes which detect the CMT duplication or by amplifying the extracted DNA and identifying the presence or absence of a DNA duplication in the amplified extension products. Also disclosed are sequences contained within the duplication used as probes for Southern analysis as well as primer sequences located within the CMT duplicated region for the PCR analysis.

20 Claims, 14 Drawing Sheets

PUBLICATIONS

Patel, P. I., et al; Genetic Mapping of Autosomal Dominant Charcot-Marie-Tooth Diseases in a Large French-Acadian Kindred: Identification of New Linked Markers on Chromosome 17; Am. J. Hum. Genet., 46:802–809 (1990).

Patel, P. I., et al; Isolation of a Marker Linked to the Charcot-Marie-Tooth Disease Type IA Gene by Differential Alu-PCR of Human Chromosome 17-retaining Hybrids; Am. J. Hum. Genet., 47–926–934 (1990).

Raeymaekers, P., et al; Localization of the Mutation in an Extended Family with Charcot-Marie-Tooth Neuropathy (HMSN I); Am. J. Hum. Genet., 45:953–958 (1989).

Ray, R., et al; Three Polymorphisms at the D17S29 Locus; Nucleic Acids Research, 18:4958 (1990).

Schwartz, D. C. and Cantor, C. R.; Separation of Yeast Chromosome-Sized DNAs by Pulsed Field Gradient Gel Electrophoresis; Cell, 37:67–75 (1984).

Shyamala, V., et al; Tandem Chromosomal Duplications: Role of REP Sequences in the Recombination Event at the Join-Point. The EMBO Journal; 9:939–946 (1990).

Southern, E. M. Detection of Specific Sequences Among DNA Fragments Separated by Gel Electrophoresis; J. Mol. Biol., 98–503–517 (1975).

Sullivan, D. E., et al; The Nucleic Acid Blot Analyzer. I: High Speed Imaging and Quantitation of $^{32}$P-Labeled Blots. BioTechniques; 5:672–678 (1987).

Timmerman, V., et al; Assignment of the Charcot-Marie-Tooth Neuropathy Type I (CMT Ia) Gene to 17p11.2-p12. Am. J. Hum. Genet., 47–680–685 (1990).

Trask, B. J., et al; Mapping of Human Chromosome Xq28 by Two-Color Fluorescence In Situ Hybridization of DNA Sequences to Interphase Cell Nuclei. Am. J. Hum. Genet., 48–1–15 (1991).

Vance, J. M., et al; Linkage of Charcot-Marie-Tooth Neuropathy Type 1a to Chromosome 17. Experimental Neurology; 104, 186–189 (1989).

Vance, J. M., et al; Localization of Charcot-Marie-Tooth Disease Type 1a (CMT1A) to Chromosome 17p11.2. Genomics, 9:623–628 (1991).

Weber, J. L., et al; Abundant Class of Human DNA Polymorphisms Which Can Be Typed Using the Polymerase Chain Reaction. Am. J. Hum. Genet., 44:388–396 (1989).

E. C. Wright; et al; A Genetic Map of Human Chromosome 17p. Genomics, 7:103–109 (1990).

HOU88

HOU76

MOLECULAR DIAGNOSIS OF AUTOSOMAL DOMINANT CHARCOT-MARIE-TOOTH DISEASE

This invention was made with government support under Grant No. NS-27042 awarded by the National Institute of Health. The government has certain rights in this invention.

FIELD OF THE INVENTION

This invention relates to the field of molecular diagnosis of autosomal dominant Charcot-Marie-Tooth disease and more particularly to the detection of duplication within the gene locus.

BACKGROUND

Charcot-Marie-Tooth disease (CMT) is the most common inherited peripheral neuropathy in humans with involvement of both the motor and sensory nerves. CMT is characterized by variable progressive atrophy of the distal muscles of the hands and the feet. The muscular atrophy leads to an associated pes cavus foot and a claw hand deformity. The clinical signs and symptoms usually manifest by the second or third decade of life although an objective diagnosis for CMT can be made by studying electrophysiological abnormalities which are evident at a much earlier age. The disease has a prevalence rate of 1/2,500. Most families demonstrate an autosomal dominant Mendelian segregation pattern, although autosomal recessive and X-linked forms of CMT have been reported.

The molecular basis of CMT is unknown. Positional cloning strategies for CMT have been based on linkage analysis since the high frequency of the disease and the survival of patients to reproductive age and beyond has permitted identification of several multi-generational pedigrees. These studies have shown that autosomal dominant CMT with decreased nerve conductive velocity is linked to markers from the proximal region of the short arm of chromosome 17. This form of CMT1 has been called CMT1A and appears to be the most prevalent form of autosomal dominant CMT. No chromosomal anomaly indicative of genomic DNA rearrangement has been described in a CMT1A patient.

Present diagnostic methods for CMT include elecro-physiologic methods to measure the conduction of nerves, histometry to quantitative nerve fibers in nerve biopsy material and electron microscopy to examine the ultrastructure of involved nerves. The commonly used methods of electromyography, nerve conduction velocity and nerve biopsy are very expensive, painful and can cause considerable risk to the patient. The estimated cost of the complete diagnostic work-up of a patient can run greater than $5,000. The DNA based diagnostic test for CMT described in the present invention enables the physician to derive the diagnostic information from DNA isolated from peripheral blood. Obtaining the sample for a diagnosis would be at minimal discomfort, the venipuncture associated with phlebotomy, and it essentially carries no risk to the patient. This DNA based diagnostic test can be performed for less than 1/10th the cost of the present diagnostic methods.

SUMMARY OF THE INVENTION

An object of the present invention is a method for diagnosing CMT disease.

A further object of the present invention are the provision of sequences for diagnosing CMT disease.

Thus in accomplishing the foregoing objects there is provided in accordance with one aspect of the present invention a method of detecting CMT disease comprising the step of measuring the presence or absence of a DNA duplication at a gene locus associated with the CMT disease.

A further aspect of the present invention is the method of measuring the duplication comprising the steps of extracting DNA from a sample to be tested, amplifying the extracted DNA and identifying the presence or absence of a DNA duplication and the amplified extension products.

In the preferred embodiment, amplification is by the polymerase chain reaction (PCR) and a duplication is identified when there are three alleles or two copies of one of two alleles of a polymorphic $(GT)_n$ dinucleotide repeat sequence, wherein n is the number of repeats.

Additional embodiments include detecting the duplication using Southern blotting analysis and restriction enzyme digest with probes contained within the CMT duplication region. The dosage measurements are selected from the group consisting of visual examination, densitometry measurement, quantitative radioactivity and quantitative fluorescence.

The two further methods of pulsed field gel electrophoresis and fluorescence in situ hybridization (FISH) have been found to be helpful in detecting CMT disease.

Also described are the flanking sequences for a $(GT)_n$ repeat contained within the CMT duplication. These flanking sequences are useful for the PCR assay.

Other and further objects, features and advantages will be apparent and eventually more readily understood from a reading of the following specification and by reference of the accompanying drawings forming a part thereof, wherein examples of the presently preferred embodiments of the invention are given for the purpose of the disclosure.

DESCRIPTION OF THE DRAWINGS

In FIG. 2C, the Southern analysis of MspI digested genomic DNA from eight unrelated CMT patients with the probe VAW409R3 (D17S122). In FIG. 2B is Southern analysis of MspI digested genomic DNA from eight control unaffected individuals with the probe VA-409R3.

FIG. 8B is an agrose gel with regions corresponding to alleles A and B cut out and the DNA purified using gene clean.

Figure 1A:
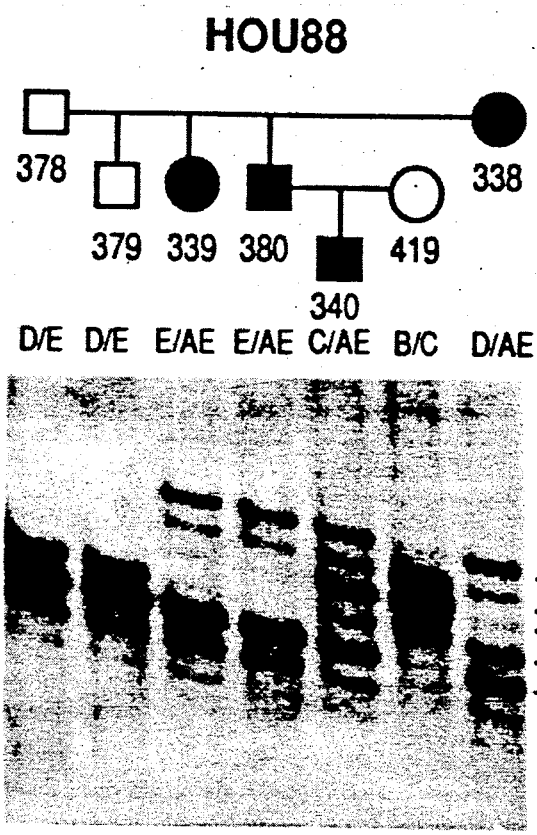
FIGS. 1(A and B) shows the detection of three alleles with the marker RM11-GT in CMT patients.

The drawings and figures are not necessarily to scale and certain features mentioned may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and the spirit of the invention.

As used herein the term "differentially labeled" indicates that each extension product can be distinguished from all others because it has a different label attached and/or is of a different size and/or binds a specifically labeled oligonucleotide. One skilled in the art would recognize a variety of labels are available. For example these can include radioisotopes, fluorescers, chemluminescers, stains, enzymes and antibodies. Various factors affect the choice of the label. These include the effect of the label on the rate of hybridization and binding of the primer to the DNA, the sensitivity of the label, the ease of making the label, primer, probe or extension of products, the ability to automate the available instrumentation, convenience and the like. For example, differential radioisotope labeling could include $^{32}P$, $^{3}H$ and $^{14}C$; differential fluorescers labeling could include fluorescein-5-isothiocyanatetetramethylrhodamine-5-(and -6) isothiocyanate, Texas Red and NBD aminohexanoic acid or a mixture of different labels such as radioisotopes, fluorescers and chemluminescers.

Each specific sample to be tested herein for its duplication in the DNA sequence is derived from genomic DNA. The source of the genomic DNA to be tested can be any medical sample. Some examples of medical samples include blood, semen, vaginal swabs, tissue, mouth wash sample, hair and mixture of body fluids.

As used herein the term "polymerase chain reaction" or "PCR" refers to the PCR procedure described in the patents to Mullis, et al., U.S. Pat. Nos. 4,683,195 and 4,683,202. The procedure basically involves: (1) treating extracted DNA to form single-stranded complementary stands; (2) adding a pair of oligonucleotide primers, wherein one primer of the pair is substantially complementary to part of the sequence in the sense strand and the other primer of each pair substantially complementary to a different part of the same sequence in the complementary antisense strand; (3) annealing the paired primers to the complementary sequence; (4) simultaneously extending the annealed primers from the 3, terminus of each primer to synthesize an extension product complementary to the strands annealed to each primer wherein said extension products after separation from their complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

As used herein "fragment thereof" refers to a partial sequence from the probe or cosmid which still identifies the polymorphism within the CMT locus.

One embodiment of the present invention is a method of detecting CMT disease comprising the step of measuring the presence or absence of a DNA duplication at a gene locus associated with CMT disease.

In a preferred embodiment of the present invention the duplication is measured by the steps of extracting DNA from a sample to be tested, amplifying the extracted DNA, identifying the presence or absence of a DNA duplication in the amplified extension products. The presence of a DNA duplication indicates that the sample came from an individual with CMT disease.

In the preferred embodiment the amplification is by the polymerase chain reaction and the primers are those identified as Sequence ID No. 2 and Sequence ID No. 3.

The CMT disease usually detected by identification of a duplication is that classified as type A. The duplication is identified as three alleles or two copies of one of two allels of a polymorphic $(GT)_n$ dinucleotide repeat sequence where n is the number of repeats. At the CMT locus, n is usually 12 to 33. For RM11-GT n is usually 13 to 19.

Alternate embodiments of the invention are available to measure the duplication. These include dosage measurements of a Southern blotting analysis of restriction enzyme digests with probes contained within the CMT duplication region. In the preferred embodiment of this method the probe comprises the sequences or fragments thereof from VAW409 (Sequence ID No. 1), VAW412, EW401 and c08H4. One skilled in the art readily recognizes that once a sequence is known probes can be made to any fraction of the sequences. The fraction can be of any size, however to increase the probability that the fraction is unique it is usually in the range of greater than 10 nucleotides. The oligonucleotide used for the probe from a fraction of Sequence ID No. 1 is thus usually at least 10 nucleotides long.

Additional ways to measure dosage measurements can include differential labelling, visual examination, densitometry measurements, quantitative radioactivity and quantitative fluorescence.

A further embodiment to measure the duplication is by pulsed field gel electrophoresis. This procedure is basically that described by Schwartz, et al., Cold Spring Harbor Symp., Quant. Biol. 47:189-195 (1982). The procedure basically comprises running a standard electrophoresis gel (agarose, polyacrylamide or other gel known to those skilled in the art) under pulsing conditions. One skilled in the art recognizes that the strength of the field as well as the direction of the field is pulsed and rotated in order to separate megabase DNA molecules. Current commercial systems are computer controlled and select the strength, direction and time of pulse depending on the molecular weight of DNA to be separated.

An additional embodiment of the present invention is a method of determining the duplication by fluorescence in situ hybridization (FISH). This procedure is described in Trask, B. J., et al., Am. J. Hum. Genet. 48,1 (1991). This procedure basically involves the steps of preparing interphase or metaphase spreads from cells or peripheral blood lymphocytes. Hybridizing labelled probes to the interphase or metaphase spreads. For example, the probes can be labelled with biotin-11-dUTP or digoxigenin-11-dUTP. Using probes with mixed labels allows visualization of space, order and distance between hybridization sites. After hybridization, the labels are examined to determine the order and distance between the hybridization sites.

Another novel aspect of the present invention is identification of the sequences important for detecting CMT disease. These sequences comprise a sequence within the CMT duplication Sequence ID No. 1 and the flanking regions that are used in the PCR assay Sequence ID No. 2 and Sequence ID No. 3.

The following examples are offered by way of illustration and are not intended to limit the invention in any manner. In examples, all percentages are by weight if for solids and by volume if for liquids and all temperatures are in degrees Celsius unless otherwise noted.

EXAMPLE 1

Identification of $(GT)_n$ Sequences $(GT)_n$ sequences were identified in several markers including the polymorphic marker RM11-GT in the subclone VAW409R1 from the D17S122 locus. In this procedure a $(GT)_n$ repeat sequence was detected in an 11 kb EcoRI fragment contained in pUC18 (VAW409R1) by Southern hybridization of dot blots of the plasmid or cosmid DNA to synthetic nick-translated poly(dC-dA)·poly(dG-dT) using alpha $^{32}$P-dCTP. Hybridization was performed in 1M NaCl, 1% SDS, 10% dextran sulfate at 65° C. and the filters were washed at room temperature in a 2X SSC, 0.1% SDS solution. A positive signal indicated the presence of a $(GT)_n$ repeat sequence. Further Southern analysis of an HaeIII-digested DNA from VAW409R1 identified a 250 bp HaeIII fragment containing the $(GT)_n$ repeat sequence. This fragment was cloned into pTZ19R (pRM11-GT). Nucleotide sequence of this fragment was determined by the dideoxy chain termination method using the Sequenase kit from United States Biochemical Corporation. The repeat sequence present in pRMII-GT was $(TA)_5(GT)_{17}(AT)_8$. Analysis of 85 unrelated individuals identified at least eight different alleles which ranged in size from 153 bp to 167 bp with an observed heterozygosity of 74%.

EXAMPLE 2

Polymorphism of the D17S122 locus duplication associated with CM

Figure 1B:
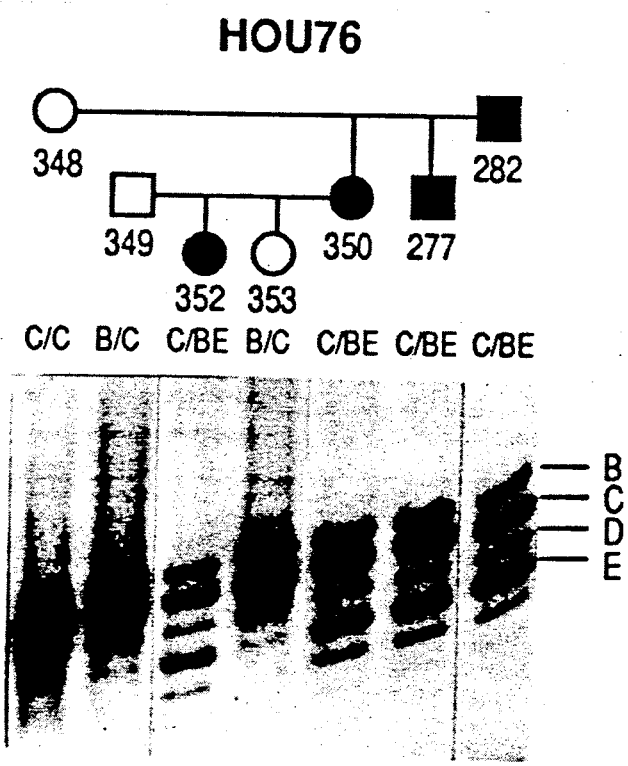

The D17S122 locus has been reported to be closely linked to the CMT disease locus and to be located in 17p11.2–17p12 region. Seven pedigrees demonstrated by linkage analysis to segregate CMT were genotyped for the $(GT)_n$ marker in RM11-GT. Representative genotypes of RM11-GT nuclear CMT families and $(GT)_n$ genotypes for members from two of these pedigrees are shown in FIG. 1. Analysis of the data in FIG. 1 reveals a striking observation. Six of eight CMT individuals showed 3 (GT) alleles (Examples: individuals 88-340, 76-352) but all unaffected individuals had either one or two $(GT)_n$ alleles. In certain matings the $(GT)_n$ genotypes were not fully informative and only two $(GT)_n$ alleles could be detected in the affected child. However, careful examination of the autoradiograph usually reveals that one of the two $(GT)_n$ alleles was present in two copies (Example: 88-339, 88-380 in FIG. 1). None of the 85 unrelated control individuals representing 170 chromosomes genotyped for this marker have displayed three $(GT)_n$ alleles at this locus. Thus, strongly indicating that this genotype is specific to CMT patients. These data demonstrate that CMT patients have three copies of the D17S122 locus.

EXAMPLE 3

Southern Analysis and Dosage Determination 5.5 μg of genomic DNA were digested with 3–4 units of the appropriate restriction endonuclease under conditions specified by the manufacturer. A 0.5 μg aliquot was examined by gel electrophoresis to determine completeness of digestion. The digested DNAs were electrophresed in a 1% agarose gel in 1X TAE buffer (40 mM Tris-HCl, pH 8.5, 40 mM sodium acetate, 2 mM EDTA) for ≈16 hrs. The DNA was transferred to a nylon membrane (Sureblot, Oncor) and hybridized to the probe after preassociation of repeats as described previously (Patel et al. 1990b). Dosage of alleles was determined by visual inspection of autoradiographs and comparison of the intensity of one polymorphic allele to the other within each lane (FIG. 2). Alternatively, such comparison was made on autoradiographs using a densitometer (LKB Ultrascan) or by direct quantitation of radioactivity in the polymorphic alleles on the nylon membrane using the Betascope analyzer (Betagen) (Sullivan et al., 1987).

EXAMPLE 4

Allele Separation for PCR Analysis

Figure 8:
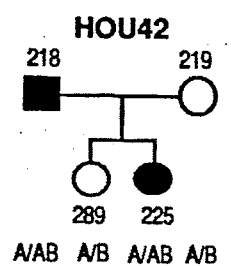
FIGS. 8(A and B) shows two $(GT)_n$ alleles in polymorphic MspI fragments with double dosage at the DI7SI22 locus.
Figure 8:
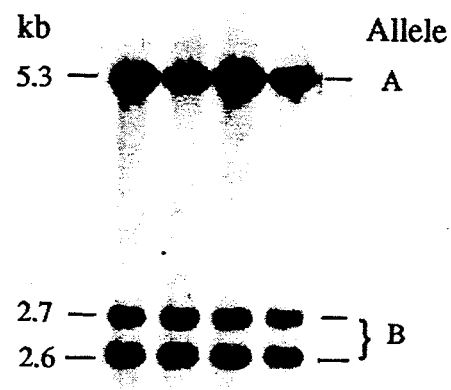
Figure 8:

Five μg of genomic DNA from members of a nuclear family in HOUS42 was digested with MspI and electrophoresed in a 1% agarose gel in 1X TAE buffer at 20 volts overnight to allow separation of 3 kb and 6 kb alleles. The gel was sliced to isolate these fractions in a minimal volume and the DNA was purified using Geneclean (BIO101). Approximately 1/30th of the isolated DNA was subjected to PCR analysis with the RM11-GT primers as described before (FIG. 8).

EXAMPLE 5

Examination of Dosage Differences Using VAW409

Figure 2A:
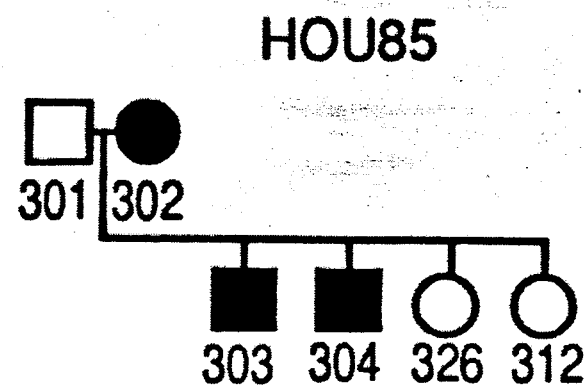
FIG. 2A shows Southern analysis of MspI digested genomic DNA from a nuclear family with the probe VAW409R3 (D17S122).
Figure 2A:
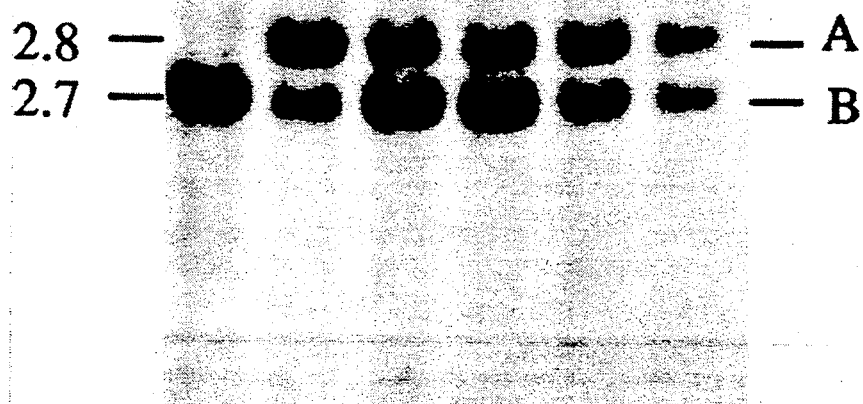
Figure 2B:
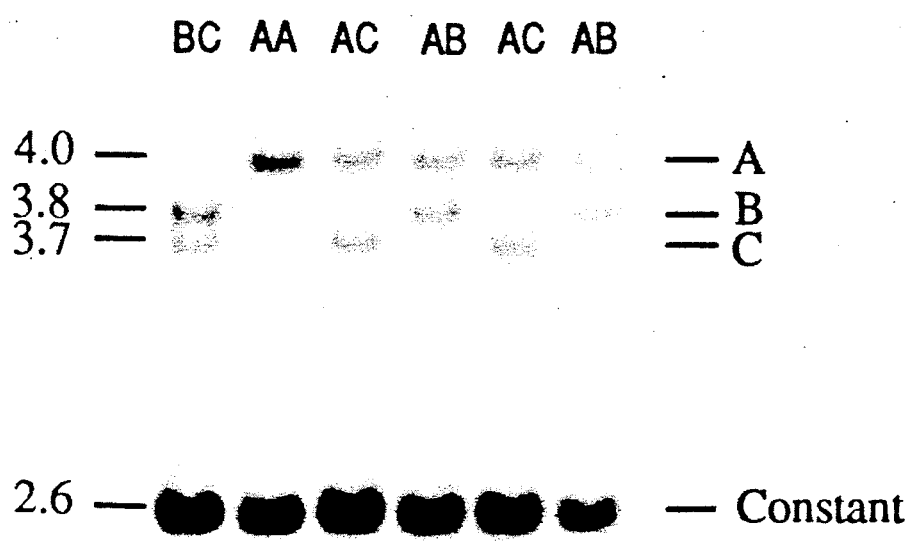
FIG. 2B shows the Southern blot from Panel A rehybridized with the control probe p10-5 representing the myosin heavy chain locus in 17p13. Panel

Dosage differences on the marker D17S122 in CMT patients by $(GT)_n$ allele was further examined by looking at polymorphic MspI alleles at this locus. Two MspI RFLPs that are associated with the marker D17S122 were genotyped. The D17S122 MspI DNA polymorphisms were detected by an 11 kb EcoRI (VAW409R1) subclone and a 2.1 kb EcoRI (VAW409R3) subclone of VAW409, and can be scored as standard two allele RFLPs. However, as shown in FIG. 2, these alleles show clear dosage differences in CMT patients. In FIG. 2A the MspI genotypes using probe VAW409R3 are illustrated in a nuclear family. The unaffected father (85-301) has genotype BB and his unaffected daughters (85-326 and 85-212) have genotype AB. The affected mother (85-302) and her affected sons (85-303 and 85-304) are all of genotype AB, however, inspection of the autoradiograph shows clear dosage differences between the two alleles. Thus, 85-302, 85-303 and 85-304 have genotypes AAB, ABB, and ABB, respectively. The VAW409R3 genotypes in FIG. 2A also demonstrate that the CMT chromosome harbors both an A and a B allele and that the AB combination segregates in a Mendelian fashion. Reprobing the same Southern blot with the distally linked control probe p10-5 (myosin heavy chain locus in 17p13) fails to demonstrate any dosage differences (FIG. 2B), confirming that the dosage alterations are specific to VAW409R3 and to CMT individuals.

As described above, these RFLPs display a dosage difference and failure to account for dosage and linkage results in false recombinants.

EXAMPLE 6

Pulsed Field Gel Electrophoresis (PFGE)

Figure 3A:
FIGS. 3(A and B) shows a novel SacII allele identified in CMT individuals by pulsed field gel electrophoresis.
Figure 3B:
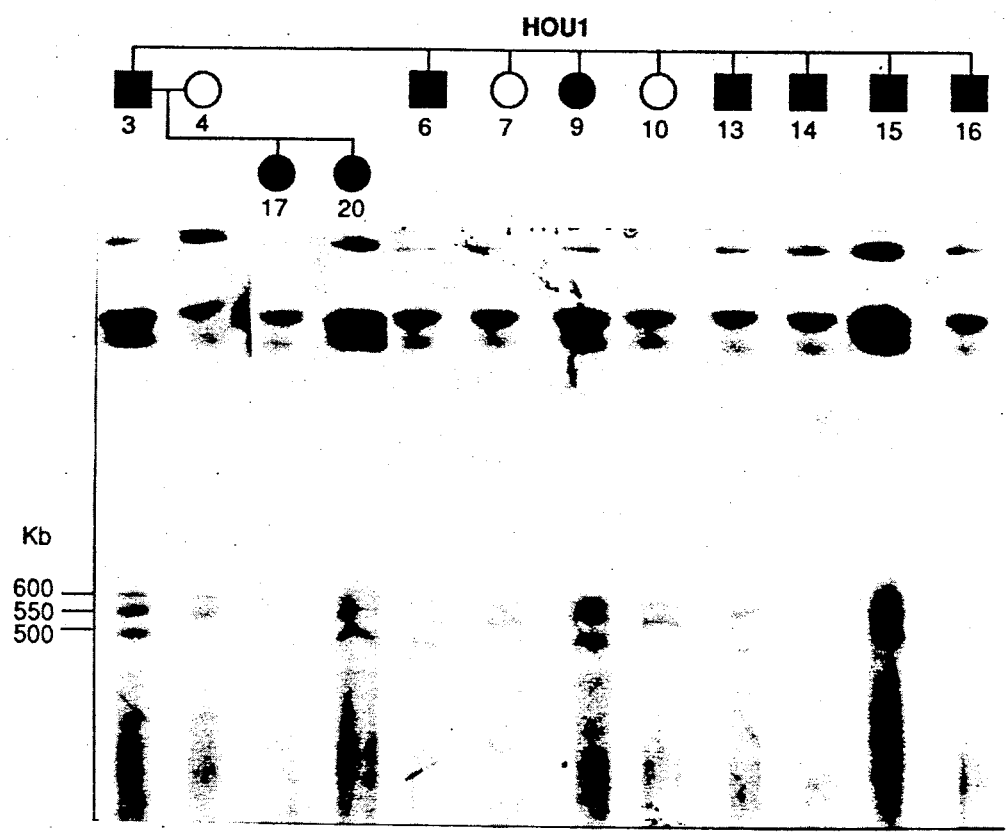
Figure 4A:
FIGS. 4(A-F) shows fluorescence in situ hybridization (FISH) of interphase nuclei from CMT and normal individuals with VAW409R3 and c1516.
Figure 4B:
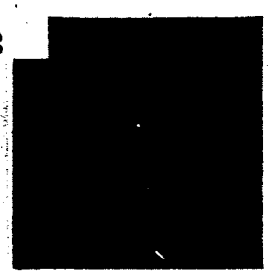
Figure 4C:
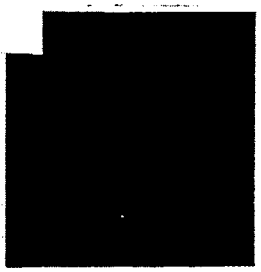
Figure 4D:
Figure 4E:
Figure 4F:
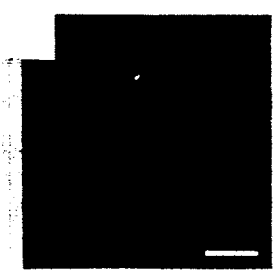

In order to more precisely define this duplication and attain an estimate of its size, long-range restriction mapping using PFGE was performed. The rare cutting restriction enzymes NotI, MluX, SacII and NruI were used to digest DNA from affected and control individuals. The digests were used to identify altered and/or novel fragments in CMT patients. Two SacII fragments of 600 kb and 550 kb which are either polymorphic alleles or variants due to methylation differences were seen in 16 control individuals using VAW409R3 as a probe (FIG. 3, lanes 6–12). A novel 500 kb SacII fragment was seen in CMT patients (FIG. 3). In FIG. 3, lymphoblasts from five CMT patients (lanes 1–5) and seven unaffected control individuals (lanes 6–12) were used for preparation of plugs. Plugs were prepared as described (Hermann et al., 1987). Briefly, exponentially growing lymphoblasts were collected and counted using a hemocytometer. The cells were resuspended at $1 \times 10^7$/ml in lysis buffer I (0.1M EDTA, 0.2M NaCl, 0.01M Tris-HCl, pH 7.8) and an equal volume of 1% Incert agarose (FMC Corporation) was added. The mixture was aliquoted into plug molds kept on ice. The plugs were suspended in lysis buffer II (lysis buffer I with 1.0% N-lauryl sarcosine and 2 mg/ml proteinase K). The digestion was carried on at 50° C. for 48 hrs. The plugs were dialyzed extensively against 10 mM Tris-HCl pH 7.5, 1 mM EDTA. Approximately 1/5 of each plug (4 μg of DNA) was digested with approximately 20 units of restriction endonuclease (SacII or FspI) in 150 μl volume and electrophoresed in a CHEF-II-DR PFGE apparatus (Biorad) for 24 hours in 0.5 x TBE buffer using pulse times of 50–90 sec ramp at 200 volts. The Southern blot was hybridized with the probe VAW409R3 as previously described with the exception that 0.5 mg/ml of human placental DNA was used for preassociation of repeats in the probe. The results from the CMT patients is seen lanes 1–5. Lane 4 shows the pattern for the homozygous patient who appears to have an increased intensity for the CMT specific SacII fragment. These results show the presence of a large genomic DNA rearrangement in CMT patients and demonstrates the presence of a novel SacII fragment of similar size which can be detected by PFGE. A novel FspI fragment also was found in CMT patients.

EXAMPLE 7

Fluorescence In Situ Hybridization (FISH)

Two-color FISH applied to interphase cell nuclei provided direct visualization of the duplication of the VAW409 locus in CMT patients.

Two-color FISH was performed as described previously (Trask et al., 1991). Briefly, VAW409R1 and VAW409R3 were combined and biotinylated using a nick translation kit (BRL). The cosmid c1516 located outside the CMT duplication was similarly labeled with digoxigenin (Boehringer Mannheim). The probes were mixed and hybridized to nuclei from post-log phase but unsynchronized lymphoblasts fixed on slides after hypotonic swelling and methanol/acetic acid fixation. After hybridization, hybridization sites of biotinylated and digoxigenin-labeled probes were labeled with Texas-Red and fluorescein, respectively, by sequential incubation of slides in (i) avidin-Texas-Red, (ii) biotinylated goat-anti-avidin and sheep anti-digoxigenin antibodies, and (iii) avidin-Texas-Red and fluoresceinated rabbit-anti-sheep IgG antibodies alternated with wash steps. Slides were viewed on a Zeiss Axiophot microscope (100× magnification) through a dual band-pass filter (Omega, Brattleboro Vt.), which allows fluorescein and Texas Red to be viewed simultaneously. Slides were coded before analysis. Nuclei were scored randomly for the number of red and green hybridization sites on each chromosome. Photographs of representative nuclei were taken on 3M Scotch 640T color slide film (15–20s exposures).

With this approach the hybridization sites of two probes can be easily distinguished using different fluorochromes or using differential labelling and the sites can be resolved more readily in interphase than in condensed metaphase chromatin. To visualize the DNA duplication in CMT patients, four lymphoblastic cell lines were analyzed in a blind study by FISH. Interphase nuclei preparations were hybridized simultaneously with biotinylated probes VAW409R1 and VAW409R3 and digoxigenin labelled cosmid c1516 which maps to the 17P11.2. The hybridization sites of VAW409 and c1516 were labeled with Texas red and fluorescein respectively (FIG. 4) and viewed together through a double band pass filter. The nuclei shown are representative of predominant hybridization patterns observed in each sample. The hybridization pattern of c1516 was used as an internal control assay for the replication status of a proximal 17p region. Panels A through D represent CMT patients and Panels E and F represent unaffected control individuals.

Because DNA replication can result in double hybridization signals in interphase, c1516 was included to identify cells that contained only two single hybridization sites for this probe and therefore had not replicated the CMT region. A total of three red VAW409 sites (two near one of the c1516 DNA sites and one paired with the second c1516 site) were observed in the majority of cells from CMT patients (60%) but only in a few cells from unaffected individuals (5%). In contrast, only one VAW409 hybridization site was paired with each c1516 site in the majority of cells from unaffected individuals (85%). The difference in the hybridization pattern of patient and control samples was not due to differences in hybridization efficiency since the fraction of nuclei lacking a VAW409 signal paired with one or both c1516 sites was similar in all cell lines (9–17%). Lymphoblast from an additional three CMT patients and four control individuals were included in a blind study for determination of the ability to identify CMT patients from the relative number of hybridization sites of VAW409 and c1516. In each case, the presence of a duplicated region in CMT patients was confirmed. This study demonstrates for the first time that duplications can be efficiently detected in interphase nuclei using FISH.

EXAMPLE 8

Homozygosity For The Duplication Mutation

Figure 5:
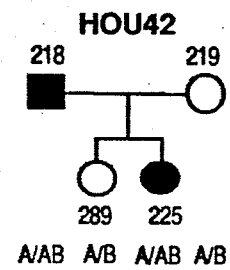
FIGS. 5(A and B) shows the results of $(GT)_n$ analysis of chromosome 17 homologues separated in somatic cell hybrids in a homozygous CMT patient.
Figure 5:
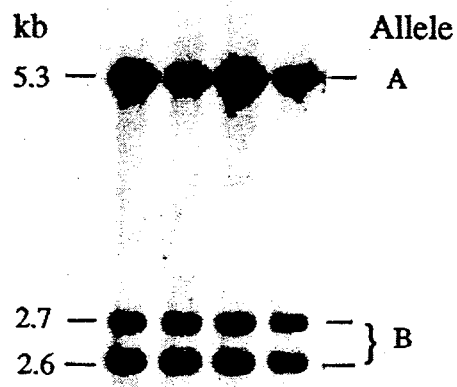
Figure 5:

A small nuclear family in which a mating occurred between two CMT affected individuals, was analyzed (FIG. 5). One of the two affected offspring of this mating (42-333) demonstrated a severe clinical phenotype including early onset (<1 year), and markedly reduced motor nerve conduction velocity (10 msec$^{-1}$ compared with 20-40 msec$^{-1}$ among affected individuals; unaffected >40 msec$^{-1}$). From the Mendelian segregation pattern of the complete pedigree it was known that the (GT) alleles A and E segregate with CMT in the families of both the affected mother and father. The $(GT)_n$ genotype of individual 42-333 is AE which suggested that she inherited a CMT chromosome from each of her parents. Her sister 42-332 has inherited one chromosome with the duplication genotype AE and has a less severe clinical phenotype.

To further confirm the conclusions made by genetic analysis and to demonstrate that the patient 42-333 had a duplication at the D17S122 locus on each of her chromosome 17s, somatic cell hybrids retaining individual chromosome 17 homologues from patient 42-333, her affected mother (42-331) and her less severely affected sister (42-332) were constructed. Lymphoblasts from the patient and mother were fused with the thymidine kinase-deficient hamster fibroblast line a23. Hybrid clones retaining one or more human chromosome 17s were selected by growth in medium containing HAT ($1 \times 1^{-3}$M hypoxanthine, $1 \times 10^{-5}$M aminopterin and $1 \times 10^{-4}$M thymidine). Positive clones from each fusion were screened for the identity of the chromosome(s) 17 retained by PCR analysis for the cell lysate with primers to a polymorphic locus in 17p (FIG. 5B). Lysate from clones retaining each of the two chromosome 17 homologues was analyzed for the $(GT)_n$ polymorphism at the D17S122 locus. The $(GT)_n$ genotypes of total DNA from each individual is displayed in the lane identified with the individual numbers while that from each corresponding pair of hybrids is shown in lanes marked a and b, respectively. The disease segregates with the $(GT)_n$ alleles A and E in the families of both the mother and the father of patient 42-333. These results clearly show that while the sister (42-332) and mother (42-331) are heterozygous with respect to the disease chromosome, the patient 42-333 is homozygous for the disease chromosome. The pedigree symbols reflect the scoring of the genotype with respect to the disease allele. These hybrids were genotyped for RM11-GT and the results (FIG. 5) confirm the following: (i) patients 42-331 and 42-332 are heterozygous for the chromosome displaying the duplication which is associated with the disease, (ii) patient 42-333 is homozygous for the duplication segregating with the disease and each chromosome 17 homologue contains two copies of the D17S122 locus.

This observation that a severely affected CMT individual homozygous for the duplicated marker and the demonstration of a perfect correlation between the presence of three alleles and the CMT phenotype indicated that the duplication is the recognizable molecular trait associated with CMT.

EXAMPLE 9

Detection Of Three Alleles With The Marker RM11-GT In CMT Patients

In order to screen the RM11-GT locus for polymorphisms either the GT strand (SEQ. I.D. No. 2) or CA strand (SEQ. I.D. No. 3) oligonucleotide primer was end-labeled at 37° C. in a 15 μl reaction volume containing 1.2 μM primer, 100 μCi of $^{32}$P ATP at 6000 Ci/mmol, 1X One Phor-All Plus buffer (Pharmacia) and 10 units polynucleotide kinase (Pharmacia). The kinase was inactivated at 65° C. for 10 min and the primer used directly without separating the unincorporated nucleotides, in the PCR reaction (0.4 μl/reaction). PCR was performed using standard conditions in a 25 μl reaction volume in a mixture containing 1 μM of each oligodeoxynuoleotide primer, 250 μM each of dATP, dCTP, dGTP, and dTTP, 2.5 μl 10X PCR buffer (500 mM KCl, 120 mM Tris HCl, pH 8.0, 1.5 mM MgCl$_2$, and 0.01% gelatin), 0.63 units of AmpliTaq (Cetus) DNA polymerase, and 0.4 μl end-labeled GT primer reaction mix. The amplification conditions included an initial denaturation of 94° C. for 5 min followed by 30 cycles of 94° C. denaturation for 1 min, 55° C. annealing for 1 min and 72° C. extension for 2 min in an automated thermal cycler (Perkin-Elmer/Cetus). Reaction products (1.5 μl) were mixed with 2 μl formamide stop solution (United States Biochemical Corporation) and electrophoresed in a 6% polyacrylamide DNA sequencing gel at 40 watts for 3.5 hrs. Gels were dried and autoradiographed for 2-12 hrs by exposing them to Kodak XAR-5 film at −70° C.

$(GT)_n$ genotypes obtained by PCR analysis were scored for the number of visible alleles using a standardized coding where allele A=165 bp, B=163 bp, D=159 bp, E=157 bp, F=155 bp and G=153 bp. When a single allele was evidence in an individual, it was scored as being present in two copies. The genotypes are indicated below the pedigree and the slash is an indication of the pair of alleles segregating with CMT in each nuclear family. As seen in FIG. 1, panel A represents a nuclear family where CMT patents 88-338 and 88-340 exhibit three (GT) alleles. The patients 88-339 and 88-380 are partially informative with respect to the number of $(GT)_n$ alleles but the higher intensity of allele E in each of these patients indicated a double dose for this allele. Panel B shows inheritance of three alleles in CMT patients from different genetic backgrounds.

Figure 6:
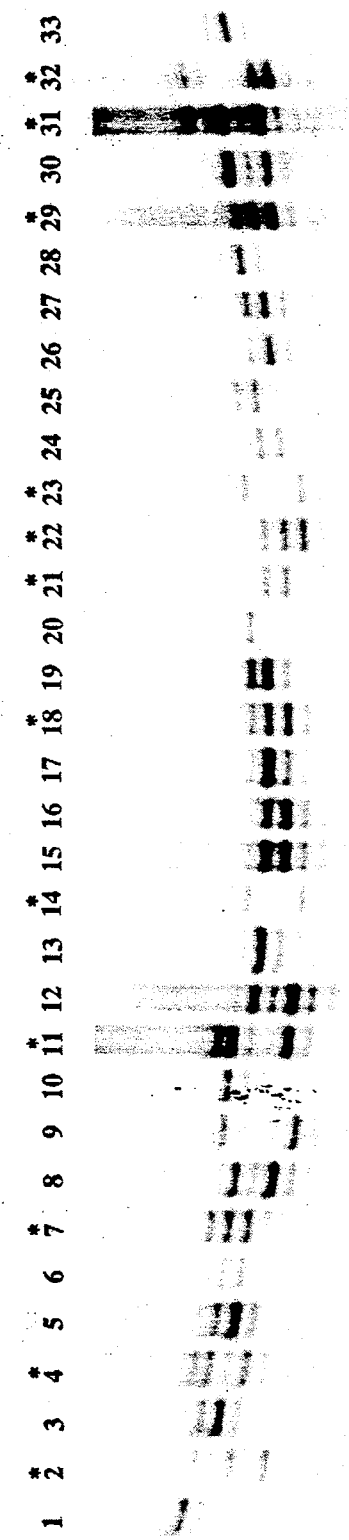
FIG. 6 shows the CMT diagnostic potential of the marker RM11-GT.
Figure 7:
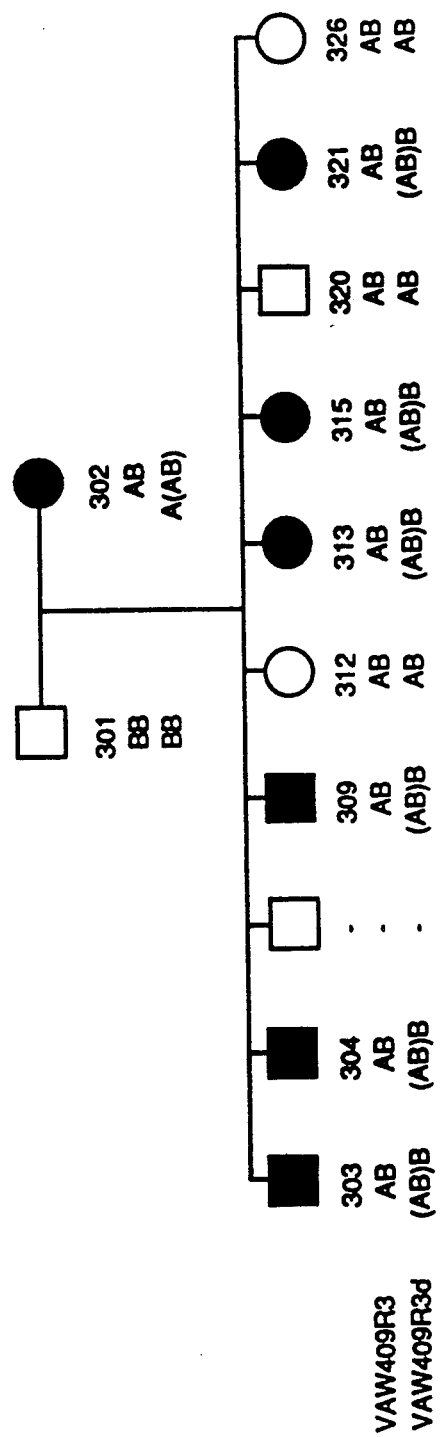
FIG. 7 shows a nuclear family where use of the VAW409R3 MspI RFLP, without accounting for dosage differences of the polymorphic alleles, misclassifies individuals.

The marker RM11-GT was tested for its potential as a diagnostic tool for CMT. Thirty-three unrelated patients with a clinical diagnosis of CMT were genotyped for this $(GT)_n$ polymorphism. The results shown in FIG. 6 indicate that 12/33 of these patients (36%) showed three alleles. Inspection of the individuals demonstrating two alleles showed a dosage difference in the majority of cases.

EXAMPLE 10

Dosage Differences In RFLP Alleles of CMT Patients

Figure 2C:
FIGS. 2C and 2D show the dosage differences in RFLP alleles of CMT patients detected by VAW409R3.
Figure 2D:
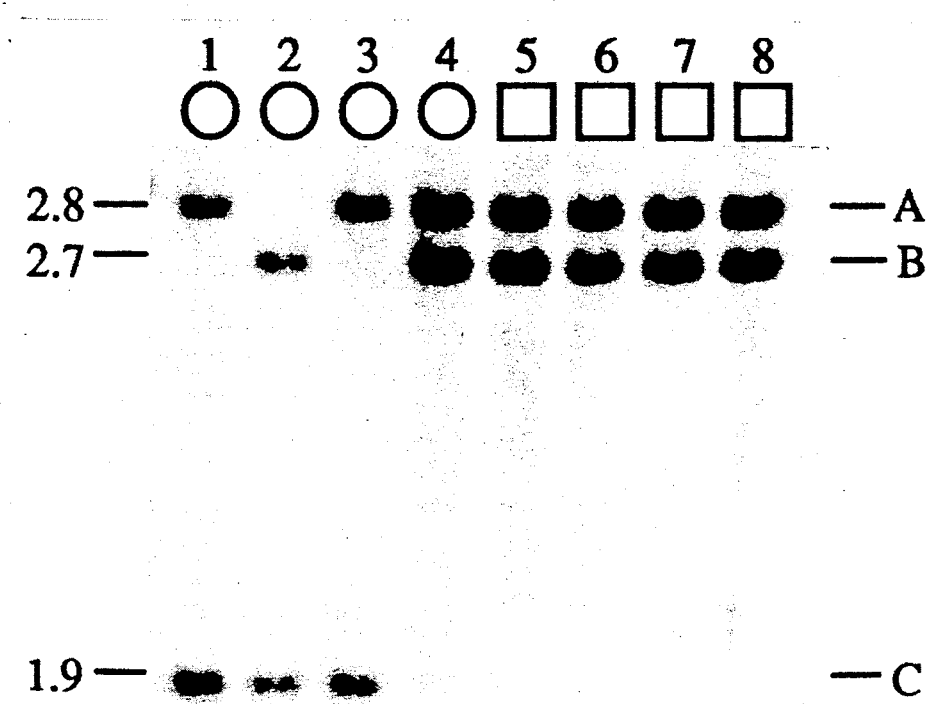

Southern analysis of MspI-digested genomic DNA from eight unrelated CMT patients with the probe VAW409R3 (D17S122) is seen in FIG. 2C. Southern analysis was conducted on five ug of genomic DNA. ■=affected male and ●=affected female. Note the presence of three polymorphic alleles in lanes 1-3 (genotype ABC). This genotype clearly illustrates the duplication but was observed in only 3/131 CMT patients. Lanes 4-6 (genotype ABB) and 7-8 (genotype AAB) show individuals who had two polymorphic alleles and in whom a duplication could be discerned by noting the difference in the relative intensity of one allele when compared to that of the other allele. Three copies of the allele could also be noted in affeoted individuals of AAA or BBB genotypes when a signal from the control probe was used for normalization. Southern analysis of MspI-digested genomic DNA from eight control individuals with the probe VAW409R3 is shown in FIG.

2D. Note the lack of dosage difference between alleles in all individuals. The Southern blot from panel B was rehybridized with a control probe p10-5. No difference in the intensity of alleles of this polymorphism was noted.

Observation of dosage of polymorphic alleles within the CMT duplication was confirmed by examination of 103 CMT patients from seven kindreds, as well as 26 other unrelated patients by Southern analysis with VAW409R3. Dosage of alleles was determined by visual examination and densitometry of autoradiographs or by quantitation of total radioactivity in each allele using a betascope analyzer. Dosage was determined only in individuals who were heterozygous for the RFLP locus. 76 of 129 CMT patients who were heterozygous for this RFLP were conclusively demonstrated to have three copies of the D17S122 locus. In contrast, none of the 63 control individuals who were heterozygous for this marker showed dosage differences for this RFLP. The control group includes 27 unaffected at risk individuals with normal NCV and 37 controls with no family history of CMT.

These RFLPs display a dosage difference and failure to account for dosage and linkage results in false recombinants.

EXAMPLE 11

A 17P Marker From Cosmid c08H4 Shows Dosage Differences

Figure 10:
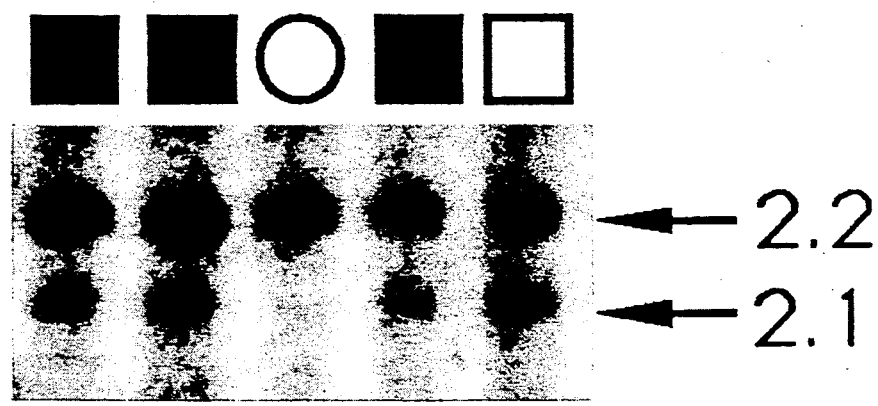
FIG. 10 shows the CMT1A duplication detected by c08H4-R2.

The cosmid c08H4-R2 from 17p11.2–17p13 contains at least eight EcoRI fragments of 8.5, 8.0, 6.5, 4.8, 2.5, 2, 1.8 and 1.3 kb and several smaller fragments. The second EcoRI fragment (c08H4-R2) detects two RFLPs which display a dosage difference only in CMT patients. These RFLPs are TaqI allele A (2.2 kb) and allele B (2.1 kb) (FIG. 10).

Cosmid c08H4 was identified in the following manner. A yeast artificial chromosome (YAC) (A217H6) of 550 kb was identified from the human genome YAC library constructed at Washington University in St. Louis, Mo. using PCR screening of pooled YAC clones with the primers from VAW409RI (SEQ. ID. Nos. 2 and 3). The end of the YAC was obtained by Alu-vector PCR to yield fragment FVG11. DNA fragment FVG11 was hybridized to a cosmid library. This cosmid library was constructed using flow-sorted human chromosome 17 DNA and thus represents a library of human chromosome 17 genetic material. FVG11 was used as a probe on this cosmid library and identified cosmid c08H4. This cosmid was demonstrated to be located in 17p11.2-p12 using mouse/human chromosome 17 somatic cell hybrids. A 2.2 kb/2.1 kb TaqI polymorphsm was identified using an 8 kb EcoRI restriction fragment from c08H4, c08H4-R2. To do this, c08H4-R2 was used as a probe in Southern analysis of genomic DNA from several individuals digested with various restriction endonucleases. The probe c08H4-R2 was then used as a probe on CMT patients and unaffected individuals. Only CMT patients demonstrated dosage differences of the TaqI polymorphism bands recognized by c08H4-R2.

EXAMPLE 12

CMT Diagnostic Potential of The Marker RM11-GT

DNA from thirty-three unrelated CMT patients was used for PCR amplification of the $(GT)_n$ alleles at the D17S122 locus. The displayed products show that 12/33 of the patients identified by asterisks revealed three $(GT)_n$ alleles thus, providing correlation of the genotype for this marker with CMT.

Figure 9:
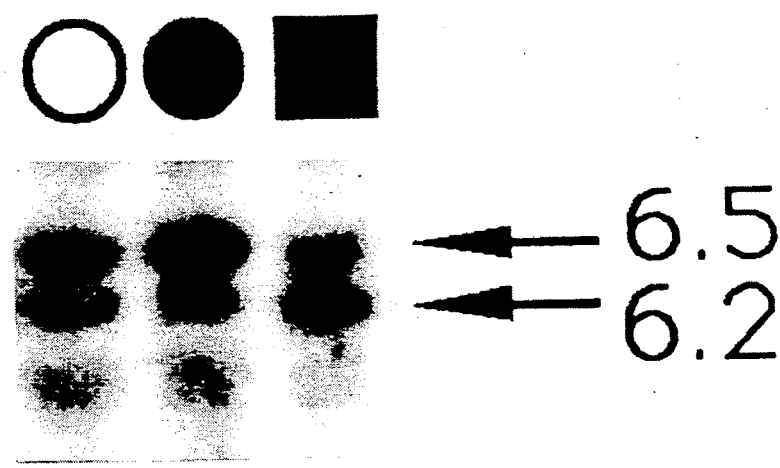
FIG. 9 shows the CMT1A duplication detected by EW401 (D17561).

It has been demonstrated that CMT is associated with a DNA duplication by several approaches which include analysis of (GT) and RFLP polymorphisms, FISH and isolation of parental chromosomes in somatic cell hybrids. Four polymorphic markers at the D17S122 locus have displayed this duplication namely, VAW409R3, VAW409R1, RM11-GT and c08H4. In each case, there is a perfect correlation between the duplication genotype and the CMT disease phenotype. PFGE and FISH suggest that the duplication includes a large genomic region of at least 500 kb. Preliminary data by RFLP analysis and dosage of polymorphic alleles indicate that additional markers VAW412R3 (D17S125) and EW401 (D17S61) (FIG. 9), which are closely linked to VAW409 are also duplicated; while other CMT-linked markers do not appear to show evidence for duplication.

Several lines of evidence suggest that the duplication discussed herein is responsible for the CMT phenotype. First, the duplication mutation was observed only in CMT patients and not observed in 63 control individuals who were examined for dosage differences by Southern analysis. Second, the duplication was demonstrated in CMT patients of different genetic backgrounds. Third, a severely affected offspring of a mating between two affected individuals, was shown to be homozygous for the duplication associated with CMT.

An important consequence of the identification of a highly polymorphic marker for CMT is the ability to confirm a clinical diagnosis of CMT with the $(GT)_n$ polymorphism. With the determination of dosage at the D17S122 locus in partially informative CMT patients, the positive predictive value of this DNA-based diagnostic test increases dramatically. Furthermore, the novel SacII fragment observed by PFGE analysis of lymphoblasts or fresh lymphocytes as well as two-color FISH are useful diagnostic methods for CMT especially when patients are not fully informative for the $(GT)_n$ polymorphism.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and attain the ends and advantages mentioned as well as those inherent therein. The sequences, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the appended claims.

What is claimed is:

1. A method of detecting Charcot-Marie-Tooth-1A(CMT-1A) disease in a sample containing DNA from an individual to be tested comprising the step of measuring the presence or absence of a DNA duplication at a gene locus associated with CMt-1A disease.

2. The method of claim 1, wherein the duplication is measured by the steps of:
   extracting DNA from a sample to be tested;
   amplifying the extracted DNA; and
   identifying the presence or absence of
   DNA duplication in the amplified extension products.

3. The method of claim 2, wherein the amplification is by the polymerase, chain reaction (PCR) and the primers are the isolated DNA of SEQ ID. No. 2 and SEQ ID. No. 3.

4. The method of claim 2, wherein the duplication is identified by the presence of three alleles or two copies of one of two alleles of a polymorphic $(GT)_n$ dinucleotide repeat sequence wherein n is the number of repeats and wherein n ranges between 12 and 33.

5. The method of claim 4, wherein n ranges between 13 and 19.

6. The method of claim 4, wherein n equals 17.

7. The method of claim 1, wherein the duplication is determined by dosage difference of polymorphic alleles measured by Southern blotting analysis of restriction enzyme digests with probes contained within the CMT-1A duplication region.

8. The method of claim 7, wherein the probe is selected from the group consisting of the sequences or a fraction thereof from VAW409, VAW412, EW401 and c08H4.

9. The method of claim 7, wherein the dosage measurement is selected from the group consisting of visual examination, densitometry measurement, quantitative radioactivity and quantitative fluorescence.

10. The method of claim 1, where the duplication is determined in a sample to be tested by pulsed field qel electrophoresis.

11. The method of claim 1, wherein the duplication is determined by fluoresoence in situ hybridization (FISH).

12. As a composition of matter, the isolated DNA consisting of SEQ ID. No. 1.

13. As a composition of matter, the isolated DNA consisting of SEQ ID. No. 2.

14. As a composition of matter, the isolated DNA consisting of SEQ ID. No. 3.

15. A kit for detecting CMT-1A disease, comprising a container and the isolated DNA consistingof SEQ ID. No. 2 and ID. No. 3.

16. The kit of claim 15, further including control of isolated DNA.

17. A kit for detecting CMT-1A disease, comprising a container and a probe which specifically hybridizes to the duplicated region of the CMT-1A locus.

18. The kit of claim 17, wherein the probe is selected from the group consisting of the isolated DNA or a fraction thereof from VAW409, VAW412, EW401 and c08H4.

19. A probe for detecting CMT-1A disease, said probe
   comprising a cosmid c08H4 or fragment thereof and characterized by:
   hybridizes with sequences located on chromosome 17 at location p11.2 to p12;
   identifies TaqI polymorphism sequences; and
   includes an 8 kb EcoRI fragment.

20. The probe of claim 19, wherein a 8 kb EcoRI fragment of c08H4 called c08H4-R2, identifies a TaqI polymorphism of 2.2 kb and 2.1 kb.

* * * * *

UNITED STATES PATENT AND TRADEMARK OFFICE
CERTIFICATE OF CORRECTION

PATENT NO. : 5,306,616
DATED : April 26, 1994
INVENTOR(S) : James R. Lupski, et al.

It is certified that error appears in the above-indentified patent and that said Letters Patent is hereby corrected as shown below:

Column 2, line 55, change "VA-409R3" to -- VAW409R3 --.

Column 3, line 5, change "DI7SI22" to -- D17S122 --.

Column 4, line 50, change "al.," to -- al.,--.

Column 5, line 49, change "CM" to -- CMT --.

Column 6, line 48, change "MspI" to -- MspI --.

Column 7, line 13, change "MIuX," to -- M1uX,--;

line 59, change "VAW409locus" to -- VAW409 locus --.

Column 10, line 32, change "(GT)" to -- $(GT)_n$ --;

line 64, change "affeoted" to -- affected --.

Column 11, line 48, change "AIu-vec-" to -- Alu-vec- --.

Column 12, line 12, change "(GT)" to -- $(GT)_n$ --.

Column 15, line 17, move "ucts" to line up under "DNA" in line 16 above;

line 19, remove the comma after "polymerase".

UNITED STATES PATENT AND TRADEMARK OFFICE
CERTIFICATE OF CORRECTION

PATENT NO. : 5,306,616
DATED : April 26, 1994
INVENTOR(S) : James R. Lupski, et al.

It is certified that error appears in the above-indentified patent and that said Letters Patent is hereby corrected as shown below:

Column 16, line 20, change "consistingof" to -- consisting of --;
    line 33, beginning with "compromising", move line up next to the end of line 32 ending with "probe" and reformat.

Signed and Sealed this

Twenty-seventh Day of December, 1994

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
　　　　( A ) LENGTH: 258 base pairs
　　　　( B ) TYPE: nucleic acid
　　　　( C ) STRANDEDNESS: double
　　　　( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
　　　　( A ) ORGANISM: RM11-GT ( v i i ) IMMEDIATE SOURCE:
　　　　( B ) CLONE: pRM11-GT ( v i i i ) POSITION IN GENOME:
　　　　( A ) CHROMOSOME/SEGMENT: 17
　　　　( B ) MAP POSITION: 17p11.2-p12

( x i ) SEQUENCE DESCRIPTION: SEQ ID NO:1:

```
GGCCAGACAG ACCAGGCTCT GCTCTACTTA AATAATCTTT ATGTATATAT ATATNCACAC      60

ACACACACAC ACACACACAC ACACACACAT ATATATATAT ATATAAATAA ACTGTGGTAG     120

CTTTATTTGT ATTTGAATGC AAGACATTTT GTGGTTCTGT AATTCCAAAA AAAAGAAGAA     180

AGAAAGAGAA AGAGTGACTT CAGCAGAACA GCTCTCTGCA ATCAGCCAAG AACAAGGAAA     240

CTGGGAGTGA AATAGGGC                                                   258
```

( 2 ) INFORMATION FOR SEQ ID NO:2:

( i ) SEQUENCE CHARACTERISTICS:
　　　　( A ) LENGTH: 22 base pairs
　　　　( B ) TYPE: nucleic acid
　　　　( C ) STRANDEDNESS: double
　　　　( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

```
GGCCAGACAG ACCAGGCTCT GC                                               22
```

( 2 ) INFORMATION FOR SEQ ID NO:3:

( i ) SEQUENCE CHARACTERISTICS:
　　　　( A ) LENGTH: 25 base pairs
　　　　( B ) TYPE: nucleic acid
　　　　( C ) STRANDEDNESS: double
　　　　( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:3:

```
CAGAACCACA AAATGTCTTG CATTC                                            25
```